United States Patent [19]

Hjertman

[11] Patent Number: 5,232,459
[45] Date of Patent: Aug. 3, 1993

[54] MULTI-DOSE SYRINGE

[75] Inventor: Birger T. Y. Hjertman, Vällingby, Sweden

[73] Assignee: Kabi Pharmacia AB, Sweden

[21] Appl. No.: 720,843

[22] PCT Filed: Jan. 4, 1990

[86] PCT No.: PCT/EP90/00014
§ 371 Date: Aug. 28, 1991
§ 102(e) Date: Aug. 28, 1991

[87] PCT Pub. No.: WO90/07946
PCT Pub. Date: Jul. 26, 1990

[30] Foreign Application Priority Data

Jan. 13, 1989 [GB] United Kingdom ............ 8900763

[51] Int. Cl.$^5$ .................................... A61M 5/00
[52] U.S. Cl. ............................ 604/208; 604/211; 604/218; 604/232
[58] Field of Search .......... 604/187, 207–211, 604/218, 220, 232, 240–243

[56] References Cited

U.S. PATENT DOCUMENTS

| 2,250,467 | 7/1941 | Cole | 604/211 |
|---|---|---|---|
| 3,162,217 | 12/1964 | Poli et al. | 604/211 X |
| 3,334,788 | 8/1967 | Hamilton | 604/211 X |
| 3,815,785 | 6/1974 | Gilmont | 222/46 |
| 4,498,904 | 2/1985 | Turner et al. | 604/211 |
| 4,583,978 | 4/1986 | Porat et al. | 604/208 |
| 4,592,745 | 6/1986 | Rex et al. | 604/211 |
| 4,883,472 | 11/1989 | Michel | 604/208 |
| 4,936,833 | 6/1990 | Sams | 604/232 |
| 4,973,318 | 11/1990 | Holm et al. | 604/208 |
| 5,092,842 | 3/1992 | Bechtold et al. | 604/135 |
| 5,104,380 | 4/1992 | Holman et al. | 604/117 |
| 5,112,317 | 5/1992 | Michel | 604/208 |
| 5,114,406 | 5/1992 | Gabriel et al. | 604/136 |

FOREIGN PATENT DOCUMENTS 0268191 5/1988 European Pat. Off. .
8807874 10/1988 PCT Int'l Appl. .

Primary Examiner—C. Fred Rosenbaum
Assistant Examiner—Mark O. Polutta
Attorney, Agent, or Firm—Pollock, Vande Sande & Priddy

[57] ABSTRACT

A prefilled syringe including a vial containing a measured quantity of an injectable product is provided Adjacent an end the vial is a displaceable wall adapted to be urged by plunger means so as to expel the product from the vial through a needle. The syringe also includes a two part housing for the vial and the plunger. One of the housing parts includes a stop surface that cooperates with a pair of corresponding surfaces extending from an external surface of the plunger. The plunger stop surfaces are positioned on opposite sides of the housing part stop surface to limit the displacement of the plunger within the vial. The position of the stop surfaces on the plunger relative to the vial may be varied by rotating the threadably connected housing parts relative to each other. A click-stop mechanism provided with the housing parts permits the housing parts to be rotated relative to each other in predetermined increments. A graduated dosing ring may be rotatably mounted about the housing parts. The dosing ring may be coaxial with and rotatable relative to the housing parts and includes means to cooperate with the click-stop mechanism.

14 Claims, 2 Drawing Sheets

MULTI-DOSE SYRINGE

FIELD OF THE INVENTION

This invention relates to a pre-filled multi-dose syringe for example for the administration by injection of a drug or other pharmaceutical product. It may take various forms; for example it may be generally in the shape of a fountain-pen, or in the shape of a conventional syringe.

BACKGROUND OF THE INVENTION

The invention particularly relates to such a syringe which is constructed relatively inexpensively and is therefore intended to be discarded when the product with which it has been filled has been exhausted.

Conventional disposable syringes contain only a single dose of the drug concerned, but in certain cases multi-dose syringes are advantageous, especially where a patient has to administer doses of the drug himself over a period of time, possibly at a frequency of more than one dose per day. In such a case the total daily dose, or even the total dose for more than one day, could be contained in a single disposable syringe to be administered in stages as required.

One multi-dose syringe is described in W088/07874. It includes a housing for a phial of liquid to be injected, having adjustment means for the dose incorporating a stop to limit the stroke of a plunger for forcing the injectable liquid out of the phial through a needle. The position of the stop is variable by rotation of the adjustment means. Ratchets are provided to ensure that the adjustment means can be rotated only in one direction and that the plunger can be displaced only in one direction. A protective cap is provided for the needle and this can be removed and fitted to the opposite end of the syringe so that an indicator line on the cap can be used as a guide to assist in a zeroing dose measuring scale associated with the adjustment means. Injection is accomplished by pressing on the cap when fitted to the end of the syringe opposite the needle.

This syringe suffers from several disadvantages. Firstly, the protective cap must be removed from the needle before the dose can be set. The needle is susceptible to damage at this time and it would be preferable to be able to set the dose with the cap still fitted over the needle and thus protecting it. Also, it is difficult to carry out injection with the cap still fitted over the end opposite needle but any attempt to remove the cap prior to injection is likely to cause undesired premature discharge of liquid through the needle. Furthermore, the ratchet mechanisms employed in W088/07874 require great precision in manufacture and in practice are likely to be the source of imprecise dosing.

SUMMARY OF THE INVENTION

The multi-dose syringe of this invention is relatively simple in construction and does not involve potentially unreliable ratchet mechanisms. It incorporates an in-built dosing ring to assist in metering the dose to be injected and does not require premature removal of the protective cap for the needle.

According to this invention a pre-filled syringe comprises a phial containing a measured quantity of an injectable product, a fixed wall at one end of the phial to receive a needle, a displaceable wall at the opposite end of the phial and displaceable into the phial by means of a plunger to expel the product out of the phial through the needle, and a two-part housing for the phial and plunger in which the two parts are connected by inter-engaging screw threads and having a stop surface on one housing part co-operable with a corresponding surface on the plunger to limit displacement of the plunger into the phial, wherein the position relative to the phial of the stop surface can be varied by rotating the two housing parts relative to one another, thus controlling the distance by which the plunger can be displaced into the phial, characterised by a graduated dosing ring mounted coaxial with, adjacent to, and rotatable relative to both housing parts.

Preferably, the first housing part holds the phial and the second housing part incorporates the said stop surface, so that relative rotation of the two housing parts enables the position of the stop surface to be varied relative to the first housing part.

Preferably, however, the syringe may be arranged to deliver more than two measured doses of the drug. In such a case, the two housing parts are preferably provided with a click-stop mechanism that permits them to be rotated relative to one another in only one direction and in such a way that free rotation is possible over a certain angle whereupon further rotation can only be achieved by passing a detent where a resistance can be felt. A number (e.g. ten) of such spaced detents can be incorporated around the periphery of the housing parts, allowing the dispensing of the same number of separate doses for each complete relative rotation of the housing parts. A rotatable dosing ring, graduated in dosage units around its periphery and coaxial with and rotatable relative to the housing parts, is also provided on one of the housing parts to facilitate dispensing of the correct dose. Before use the dosing ring is rotated to align a zero mark on the dosing ring with an indicator mark on the other housing part. This other housing part is then rotated clockwise past one or more detents until the indicator mark on it is aligned with the mark showing the desired dose on the dosing ring. This results in relative telescoping together of the two housing parts over such a distance that depression of the plunger as far as possible will result in dispensing of the indicated dose.

In order to dispense the next dose, the dosing ring is first turned to align its zero mark with the indicator mark on the other housing part and the remainder of the procedure is then repeated as described in the foregoing paragraph.

The means permitting relative rotation of the two housing parts in only one direction over a number of spaced detents may comprise pawl means on one of the housing parts. This housing part is preferably the first (i.e outer) housing part within which the other, (i.e. inner), housing part is located and around the outside of which the dosing ring fits. In this case, the pawl means preferably co-operates both with a series of spaced longitudinal grooves or ribs on both the dosing ring and the second housing part, to permit independent click stop rotation of both dosing ring and first housing part relative to the second housing part, the pawl means being shaped to permit the second housing part to turn only in the direction in which it is screwed into the first housing part but, preferably, allowing the dosing ring to turn in either direction.

Especially if the syringe is to contain more than a daily dose of the drug or other product, this preferably contains a pharmaceutically-acceptable preservative. Preferably, the hypodermic needle will be discarded after each injection and replaced by a new needle prior to the following injection. Otherwise, a replaceable cap may be provided to protect the needle and keep it sterile when not in use. The needle may then be used until it begins to feel blunt to the patient so that further use of it is uncomfortable.

The phial is preferably transparent (e.g. of glass) and an opening or a transparent window, is preferably located in the wall of the housing close to the needle end in order that the user may visually check the number of doses remaining in the phial. The window or opening may have associated graduated markings to show the number of dose units remaining.

Although the phial is preferably of glass, other parts of the syringe, and in particular the two housing parts and the plunger, are preferably formed of plastics material, for example by injection moulding, to reduce cost to a minimum.

BRIEF DESCRIPTION OF THE DRAWINGS

One disposable syringe embodying the invention for administration of two equal doses of an injectable drug will now be described with reference to the accompanying drawings in which.

BEST AND VARIOUS MODES FOR CARRYING OUT INVENTION

Figure 1:
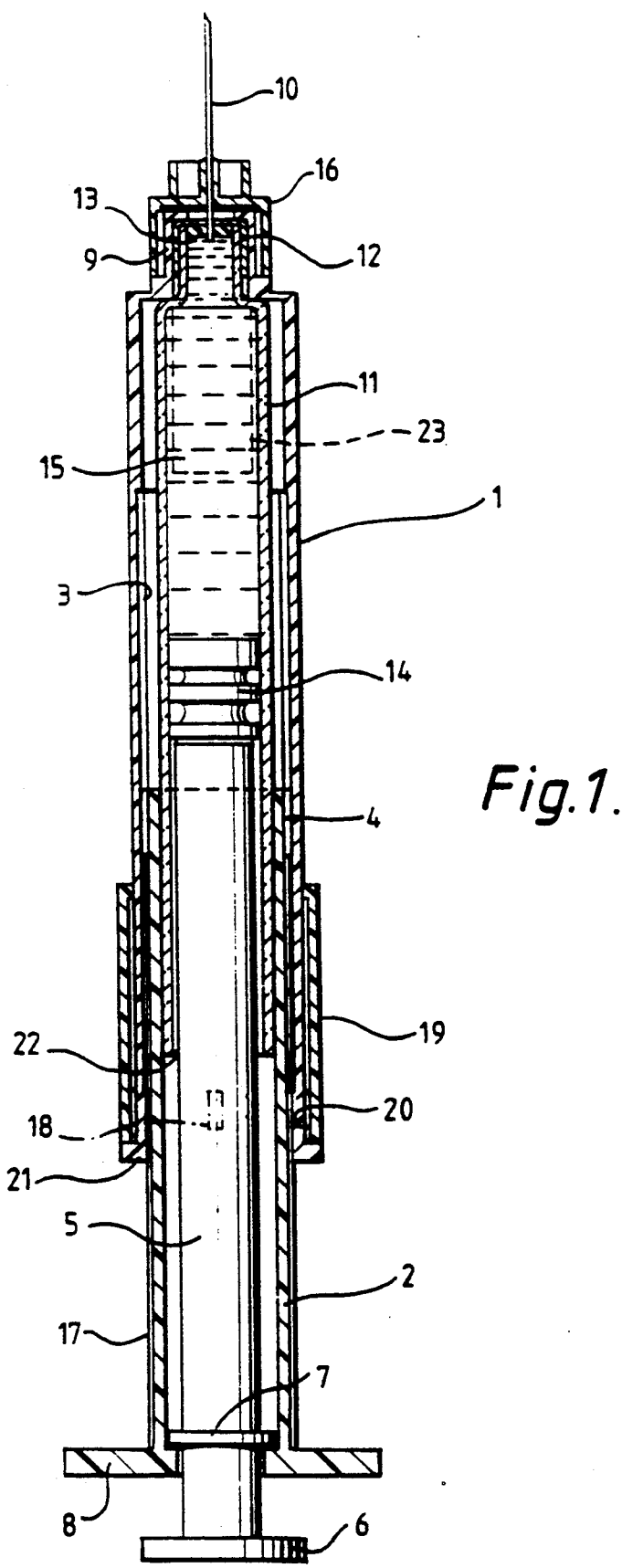
FIG. 1 is a cross-section of a syringe.

The syringe comprises a first, outer, cylindrical housing part 1 and a second, inner, cylindrical housing part 2. The first housing part 1 has an end wall 9 and has internal screw-threading 3 over a part of its whole length and the second housing part 2 has an externally threaded end 4 mating with the threading 3 on the first housing part. The inner housing part 2 has an end wall 8. The inner housing part 2 acts as a housing for a plunger rod 5 having an operating handle 6 at one end. The plunger rod 5 has an integral stop 7 spaced from the handle 6 and both the stop 7 and the inner surface of the handle 6 co-operate with the end wall to limit the travel of the plunger rod 5. The other end wall 9 of the outer housing portion is externally threaded and of reduced cross-section to receive a corresponding internally-threaded needle holder 16 provided with a hypodermic needle 10. A glass phial 11 is housed within the outer and inner housing parts 1, 2. This phial has a necked first end 12 closed by a pierced elastomeric bung 13 through which the needle passes, forming a seal. The other end 22 of the phial 11 is open and receives the plunger rod 5. The plunger rod 5 co-operates with an elastomeric piston member 14 which is slidable within the phial 11 and forms a fluid-tight seal with the inner wall thereof. The space within the phial between the piston member 14 and the bung 13 is filled with a solution of a drug 15 such as heparin.

The outer housing part 1 is provided with two opposite window openings 23 to enable the user to check the presence of drug solution, and absence of air bubbles, within the phial 11.

The area of the inner housing part 2 not provided with an external screw thread 4 has a series of longitudinal circumferentially-spaced grooves 17, one of which is specially indicated. These co-operate with the inner surface of pawl 18 carried on a resilient tongue 21 partially cut out from the wall of the outer housing part 1. The inner pawl surface is wedge-shaped so that when the inner body member 2 is rotated clockwise relative to the outer housing part 1, the pawl 18 rides over the grooves 17, emitting an audible click as each groove is traversed. Rotation in the opposite (anti-clockwise) direction is, however, resisted by the pawl.

A dosing ring 19 fits around the outside of the outer housing part 1, and is provided on its inside surface with longitudinal grooves 20 having the same angular spacing as the grooves 17. These grooves 20 co-operate with the outer surface of the pawl 18, which surface is shaped to permit click-stop rotation of the ring 19 in either direction. The ring 1 has a zero indicator mark and marks indicating different doses spaced around its periphery.

Figure 2:
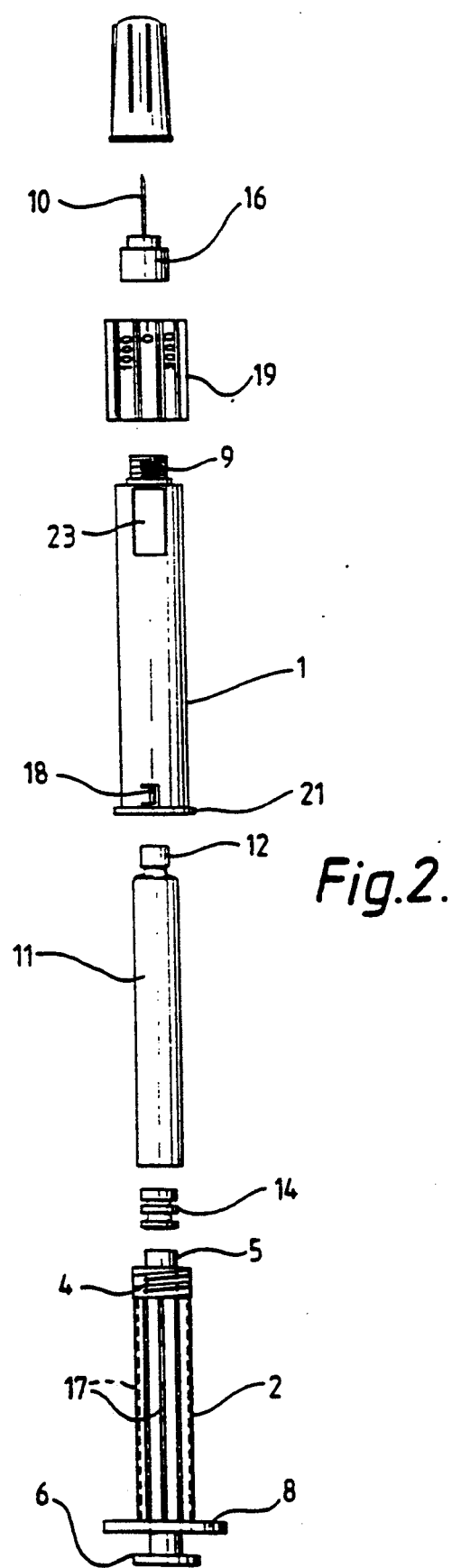
FIG. 2 is an exploded perspective view of the syringe shown in FIG. 1.

A removable protective end cap (FIG. 2) is fitted over the exposed end of the needle 10.

The syringe is supplied with the phial full of drug solution and with the piston 14 adjacent the open end 22 of the phial. The inner housing part 2 protrudes to its maximum extent from the outer body portion and the plunger rod 5 is within the inner housing part 2. The plunger rod 5 is in contact with the piston 14 which, in turn, is in contact with the drug solution inside the phial 11.

Before administering the first dose the syringe is adjusted to zero and any air is removed by screwing the needle holder 16 together with the needle 10 onto the outer housing portion 9 and the handle 6 is pressed in as much as possible towards the end wall 8 with the syringe held upwards until any air has been expelled.

To administer a desired dose of the drug solution, the dosing ring 19 is turned so that its zero mark is aligned with the indicator line on the inner housing part 2. The inner housing part is then rotated in a clockwise direction until its indicator line becomes aligned with the mark on the dosing ring that corresponds to the desired dose. This rotation of the inner housing part 2 causes it to be screwed into the inner housing part 2 for a certain distance, leaving the handle end of the plunger rod 5 projecting by the same distance from the inner housing part 2. The protective end cap is then removed, exposing the needle, and the needle is then inserted into the body into which the drug solution is to be injected. The plunger rod 5 is then pushed as far as possible into the outer body portion thus causing a measured volume of the solution to be injected into the body. The markings on the dosing ring are such that the dose injected is the dose shown on the dosing ring marking that has been aligned with the indicator line on the inner body member.

To administer the next dose, the above procedure is repeated.

I claim:
1. A prefilled syringe comprising:
a vial containing a measured quantity of an injectable product, said vial having adjacent a first end thereof a fixed wall, said fixed wall including means for receiving a hollow needle providing an opening into said vial, said vial having adjacent its second opposite end a displaceable wall urged toward said fixed wall by a plunger means so as to expel said product from said vial and through said needle said second end including an opening for receiving said plunger means;
a housing for said vial and said plunger including two threadably connectable housing parts, one of said housing parts including a stop surface extending inward from an inner surface and cooperating with a pair of corresponding surfaces extending from an external surface of said plunger, one of said plunger stop surfaces being positioned on each side of said housing part stop surface to limit the displacement of said plunger within said vial, whereby the position of said stop surfaces on said plunger relative to said vial may be varied by rotating said threadably connected housing parts relative to each other;

a click-stop mechanism provided with said two housing parts permits rotation of said two housing parts relative to each other in predetermined increments;

a graduated dosing ring rotatably mounted about said two housing parts, said dosing ring being coaxial with and rotatable relative to said two housing parts, said dosing ring including means to cooperate with said click-stop mechanism.

2. The syringe according to claim 1 wherein said two housing parts include a first outer housing part having adjacent a first end thereof a wall and adjacent its second opposite end an opening to receive a second part, said vial, and said plunger means, said first outer housing part also including an inner threaded surface;

said housing also including a second inner housing part including adjacent a first end thereof an externally threaded connection, said threaded connection engaging said inner threaded surface of said first outer housing part, said second inner housing part including said stop surface extending inward from an inner surface adjacent a second opposite end of said second part.

3. The syringe according to claim 1, wherein said click-stop mechanism includes a plurality of detents formed on a surface of one of said housing parts and parallel to a major axis of said housing part, whereby said protrusion engages said surface of said housing part.

4. The syringe according to claim 1, wherein said click-stop mechanism permits said two housing parts to be rotated relative to each other in only one direction.

5. The syringe according to claim 1, wherein said two housing parts include a first outer housing part having adjacent a first end thereof a wall and adjacent its second opposite end an opening to receive a second part, said first outer housing part also including an inner threaded surface;

said housing also including a second inner housing part including adjacent a first end thereof an externally threaded connection, said threaded connection engaging said inner threaded surface of said first outer housing part, said second inner housing part including said stop surface extending inward from an inner surface adjacent a second opposite end of said second part;

an interior wall and said wall of said first housing part holds said vial immobile and said second housing part incorporates said stop surface so that rotation of said two housing parts relative to each other enables the position of the stop surface to be varied relative to said first housing part.

6. The syringe according to claim 1, wherein said click-stop mechanism permits the rotation of said two housing parts relative to each other in only one direction and includes pawl means on one of said housing parts.

7. The syringe according to claim 6, wherein a plurality of spaced detents is provided around the periphery of the other of said housing parts to cooperate with said pawl means.

8. The syringe according to claim 7, wherein said other housing part includes ten spaced detents.

9. The syringe according to claim 6, wherein said syringe includes a first outer housing part and a second inner housing part;

said pawl being located on said first housing part;

said dosing ring surrounding said first housing part;

said second housing part having a series of spaced longitudinal detents around an outer periphery thereof and wherein said dosing ring has a similar series of spaced longitudinal detents around an inner periphery thereof;

said detents cooperating with said pawl means to permit independent click-stop rotation of said dosing ring and said second housing part relative to said first housing part;

said pawl means being shaped to permit the second housing part to turn only in the direction which causes it to be screwed into said first housing part.

10. The syringe according to claim 9, wherein said dosing ring is free to turn clockwise or counterclockwise relative to said first housing member.

11. The syringe according to claim 1, wherein injectable product contains a pharmaceutically-acceptable preservative.

12. The syringe according to claim 1, wherein said vial is transparent and an opening is located in the wall of the first housing part substantially near said first end of said vial to permit a user visually to check the number of doses remaining in said vial.

13. The syringe according to claim 1, wherein said vial is transparent and a window is located in the wall of the first housing part substantially near said first end of said vial to permit a user visually to check the number of doses remaining in the vial.

14. A prefilled syringe comprising:

a vial containing a measured quantity of an injectable product, said vial having adjacent a first end thereof a fixed wall, said fixed wall including means for receiving a hollow needle, said vial having adjacent its second opposite end a displaceable wall which is urged toward said fixed wall by a plunger means so as to expel said product from said vial and through said needle;

a housing for said vial and said plunger including a first outer housing part having adjacent a first end thereof a wall and adjacent a second opposite end an opening to receive a second inner part, said vial, and said plunger means, said first outer housing part also including an inner threaded surface and a protrusion;

said housing also including a second inner housing part including adjacent a first end thereof an externally threaded connection, said threaded connection engaging said inner threaded surface of said first outer housing part, said plunger and said vial being housed within said second inner housing part, said second housing part including adjacent a second opposite end thereof a stop surface extending inward from an inner surface, said stop surface cooperating with a pair of corresponding stop surfaces extending from an external surface of said plunger, one of said stop surfaces on said plunger being positioned on each side of said stop surface on said housing part to limit the displacement of said plunger within said vial, whereby the position of said stop surfaces on said plunger relative to said vial may be varied by rotating said threadably connected first and second housing parts relative to each other;

said housing parts having a click-stop mechanism including a plurality of detents formed on an external surface of said second housing part and parallel to a major axis of said second inner housing part, whereby said protrusion is shaped to permit rotation of said housing parts relative to each other at predetermined intervals in only one direction;

a graduated dosing ring rotatably mounted about said second end of said first outer housing part, said dosing ring being coaxial with and rotatable relative to said two housing parts, said dosing ring including means to cooperative with said click-stop mechanism.

* * * * *